United States Patent [19]

Boucher

[11] Patent Number: 4,500,530

[45] Date of Patent: * Feb. 19, 1985

[54] METHOD OF TREATING HORSES TO INHIBIT OR REDUCE INCREASES IN CRENATED RED BLOOD CELLS DURING EXERCISE

[76] Inventor: John H. Boucher, 2106 Salisbury Rd., Silver Spring, Md. 20910

[ * ] Notice: The portion of the term of this patent subsequent to May 17, 2000 has been disclaimed.

[21] Appl. No.: 421,803

[22] Filed: Sep. 23, 1982

Related U.S. Application Data

[62] Division of Ser. No. 210,591, Nov. 26, 1980, Pat. No. 4,383,997.

[51] Int. Cl.³ .......................................... A61K 31/495
[52] U.S. Cl. .................................................... 514/255
[58] Field of Search ........................................ 424/250

[56] References Cited

PUBLICATIONS

Flameng et al.-Angiology, vol. 30, No. 8, (1979), pp. 516-525.
DeCree et al.-Chem. Abst., vol. 91 (1979), p. 168,649w.
Flameng et al.-Chem. Abst., vol. 91 (1979), p. 168,650q.
Heidbreder-Chem. Abst., vol. 84 (1976), p. 69,576u.
Jageneau et al.-Chem. Abst., vol. 77 (1972), p. 70372m.
Detry et al.-Chem. Abst., vol. 85 (1976), p. 104,151w.

*Primary Examiner*—Sam Rosen
*Attorney, Agent, or Firm*—Larson and Taylor

[57] ABSTRACT

A marked increase in spiculated or crenated erythrocytes of animals such as horses following physical activity has been found. This condition is treated by administering to the animal a compound which inhibits influx of extracellular $Ca^{++}$ into red blood cells, or enhances the ATP content of ATP-depleted red blood cells.

2 Claims, 2 Drawing Figures

METHOD OF TREATING HORSES TO INHIBIT OR REDUCE INCREASES IN CRENATED RED BLOOD CELLS DURING EXERCISE

This is a division of the application Ser. No. 210,591 filed Nov. 26, 1980, now U.S. Pat. No. 4,383,997.

BACKGROUND OF THE INVENTION

This invention relates to a method of preventing and/or reducing the increased crenated or spiculated red blood cells found in the blood of animals subjected to physical activity.

It has been surprisingly discovered that in contrast to the normal population of circulating red blood cells (erthyrocytes) observed from the blood samples of resting horses, exercise induces a marked increase in the number of crenated or spiculated red blood cells in the blood of the horses. This red cell alteration that occurs in horses subjected to exercise has been previously unrecognized and its cause is presently unknown. The same increase in the percentage of crenated cells is believed to occur in other animals including humans who have undergone exercise.

An increase in red blood cell spiculation may accelerate destruction of the cells and promote a "sport anemia" analogous to that observed in humans. In addition, the spiculated cells were confirmed by scanning electron microscopy to be echinocytes which are characterized by a cell membrane of reduced deformability. The deformability of the red blood cell membrane is important in the larger arteries because it allows greater fluidity of the red cells which changes the blood into an emulsion of low apparent viscosity, but it is also of critical importance at the microcirculatory level where the red blood cells must travel through the capillaries with a smaller diameter than their own. Hence a decrease in red blood cell deformability not only increases the apparent viscosity of the blood and, thus, augments the total resistance to flow, but also reduces capillary blood flow, tissue perfusion and tissue oxygenation.

SUMMARY OF THE INVENTION

According to the present invention the increase in crenated or spiculated red blood cells which occurs in the blood of animals after exercise sufficient to induce said increase of crenated red blood cells, the blood of said animal having a normal content of crenated red blood cells prior to said exercise, is prevented or reduced by administering to said animal immediately prior, during or subsequent to said exercise an effective amount of a compound selected from the group consisting of a compound which inhibits influx of extracellular $Ca^{++}$ ions in red blood cells and a compound which increases intracellular red blood cell adenosine triphosphate (ATP) content.

DETAILED DESCRIPTION OF THE INVENTION

Figure 1:
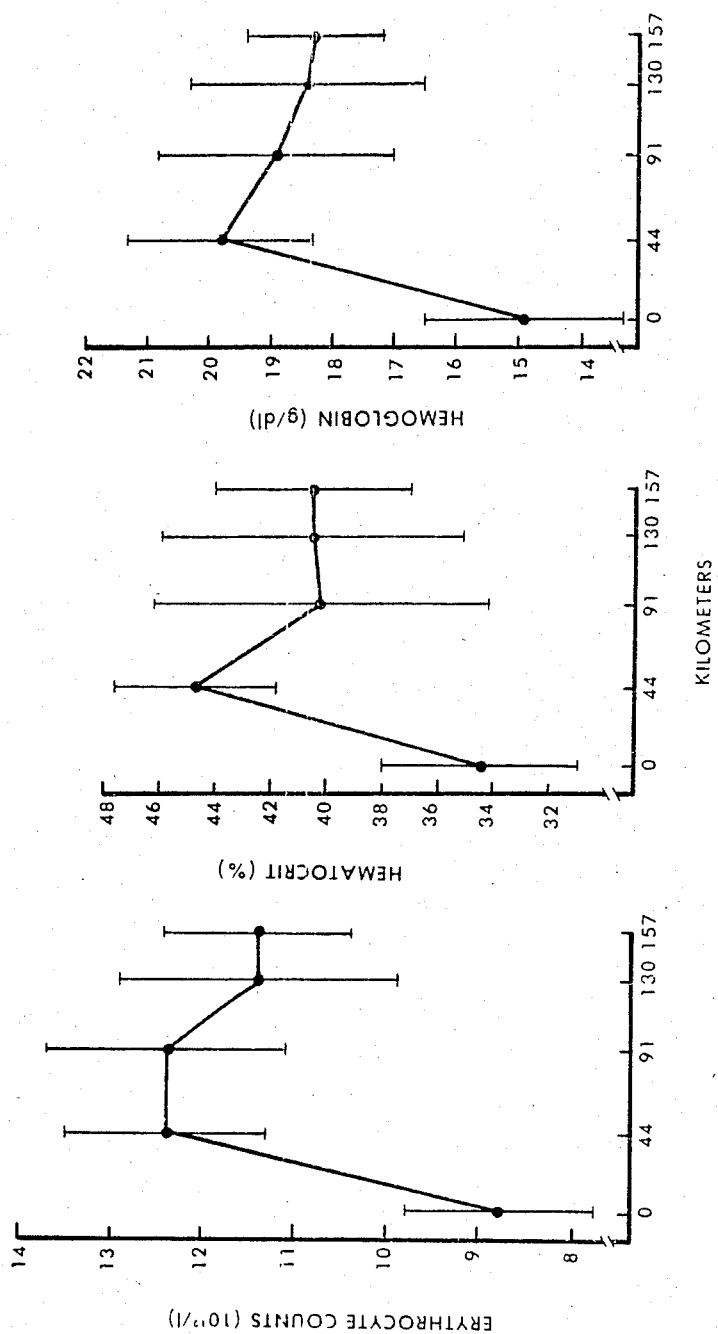

While the present invention may find greater utility when employed prophylactically, that is, in the prevention of the newly discovered condition it is equally useful in the treatment of the condition. Compounds which inhibit influx of extracellular $Ca^{++}$ into red blood cells or compounds which increase intracellular red blood cell adenosine triphosphate, in addition to preventing the increase in crenated cells, have been found to restore the cells to their normal condition. In either case, the animal is spared the reduction in capillary blood flow, tissue perfusion and tissue oxygenation that occurs during the existence of this condition, that is, for the time it takes the body to bring down the increased number of crenated cells to a normal level. Moreover, the present invention will prevent the destruction of red blood cells accelerated by the crenation.

As aforementioned, while the cause of the increase in crenated blood cells following strenuous exercise is not known, it is believed related to the existence of hypoxic conditions within the cell environment. The deformability of the cell membrane of normal red blood cells is maintained by ATP and its energy-producing ability to assist the active pumping of divalent ions, such as $Ca^{++}$, across the cell membrane to maintain normal intracellular osmolarity. At least part of the ATP is thought to play a major role in pumping $Ca^{++}$ out of the cell so as to maintain a normal balance. If the $Ca^{++}$ is not discharged from the blood cell at the normal rate, the $Ca^{++}$ content builds up within the cell and causes an alteration in the lipid composition of the red cell's membrane structure causing its decreased flexibility and promoting a spiculated morphology (crenation).

The reason for the appearance of spiculated red cells during exercise is unknown, and although speculative, it is believed that the spleen plays a major role. Because this organ (spleen) serves as the store-house for about 40–60% of a resting horse's red cell volume, and because one of the spleen's functions is to filter-out older red cells by a deformability-sensing process, and because it has an excessively stagnant and hypoxic environment compatible with conditions which could deplete red cell ATP (by inhibiting glycolytic production of ATP), it serves as a reservoir of crenated red cells. Upon exercise, the horse's spleen responds by contraction (a well-known mechanism) and expels its stored red cells into the circulation. The result is a high percentage of crenated red cells in the circulation during exercise. This mechanism would explain why a large increase of spiculated cells is observed in the circulation regardless of the duration of physical activity. The condition has been seen in horses during light workouts (running at near maximal speed for ⅝ mile) as well as during endurance exercise (100 miles).

The compounds which inhibit influx of extracellular $Ca^{++}$ into red blood cells are well known to those skilled in the art. The preferred compounds are N-cinnamyl-N'-benzhydryl piperazines having the formula:

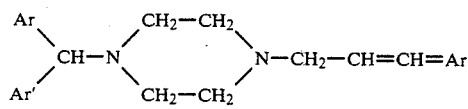

wherein Ar and Ar' are selected from the group consisting of phenyl and fluorophenyl or therapeutically active acid addition salts thereof. Illustrative of these compounds are 1-cinnamyl-4-(di-p-fluorobenzhydryl piperazine dihydrochloride, also known generically as "flunarizine" and 1-cinnamyl-4-(α-phenylbenzyl)piperazine dihydrochloride, also known generically as "cinnarizine".

Examples of other compounds known to inhibit influx of $Ca^{++}$ into red blood are 4[4,4-bis(4-fluorophenyl)butyl]-N-(2,6-dimethylphenyl)-1-piperazineacetamide known generically as "lidoflazine" and "Butenizine" (a compound of Janssen Pharmaceutica).

Compounds which increase intracellular ATP are also known to those skilled in this art. Illustrative and preferred amongst these compounds is 3,7-dihydro-3,7-dimethyl-1-(5-oxohexyl)-1H-purine-2,6-dione, generically known as "pentoxifylline".

In accordance with the present invention, effective amounts of compounds which inhibit influx of $Ca^{++}$ into red blood cells or compounds which increase intracellular red blood cell ATP are administered internally to the animal either before, during or after strenuous exercise. The actual amount administered in any given case will vary depending primarily upon the particular animal treated, the specific compound utilized and the regimen adopted. In general, however, the amount of active compound administered will fall in the range of about 0.1 to 10 mg per kilo of body weight of the animal treated. Advantageously, the active compound is administered intimately admixed with a pharmaceutically acceptable carrier which carrier can take a variety of forms depending upon the form of administration, i.e. oral, parenteral or intravenous. In oral administrations the pharmaceutically acceptable carriers usually comprise for example, water, glycols, oils, alcohols in the case of liquid preparations and starches, sugars, kaolin, lubricants, binders and the like in the case of solid preparations such as powders, capsules and tablets. In preparations for parenteral or intravenuous injection the pharmaceutical media is usually sterile water, saline solution, glucose solution and mixtures thereof. Injectable suspensions may also be used in which case appropriate liquid carriers, suspending agents and the like may be employed. The administration of the active compound of the invention is effected immediately before, during or immediately after the exercise so as to ensure the activity of the compounds. In those instances where the animal is going to participate in a strenuously active event for which optimal tissue oxygenation is imperative, it is preferred that the active compound be administered at regular intervals over a period of time as, for instance, by a daily administration for at least 7 days prior to the event. In addition, the active ingredient should be administered sufficiently in advance of a practice workout so that the highest blood level of the active ingredient coincides with the actual workout. In such a manner of treatment, when the spleen empties during exercise it will refill after exercise with red cells and plasma highly concentrated with the active ingredient. Consequently, the site of potential ATP depletion of red blood cells, i.e. the spleen, is provided with maximum possible concentrations of administered active ingredient for prevention of crenation. Administrations rendered too far in advance of or too far after the exercise should be avoided for this reason. In instances where prior treatment has not been given and rapid results are desired, the compounds are generally administered intravenously within about 4 hours of the exercise.

DISCOVERY OF THE CONDITION

Figure 2:
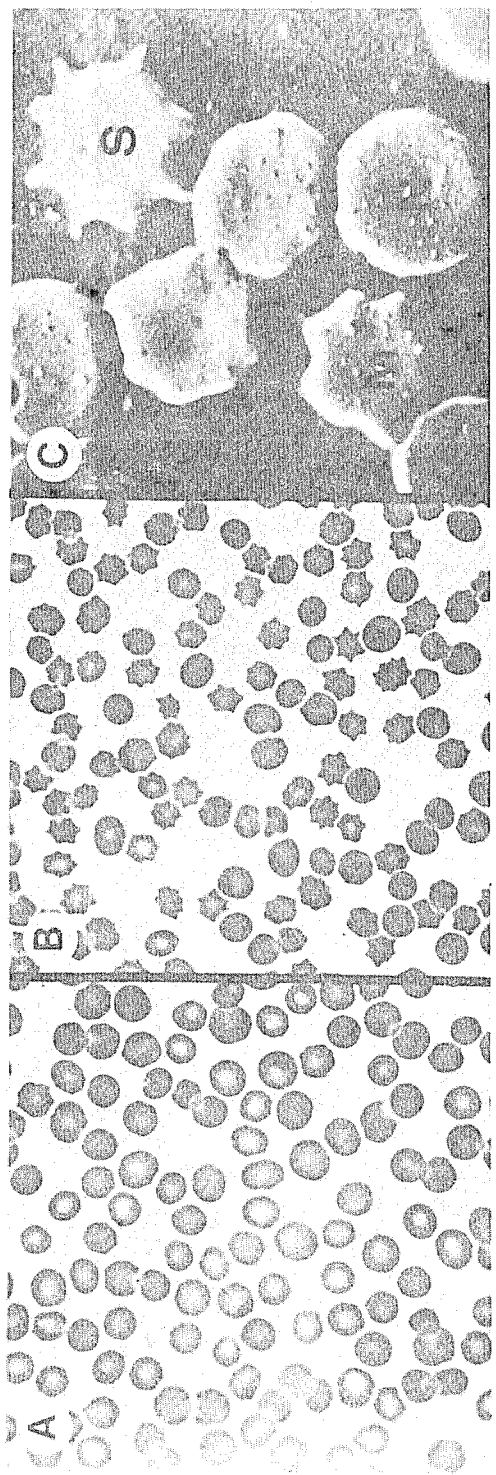

The experiments reported below make reference to the drawings wherein:

FIG. 1 represents the erythrocyte count, hematocrit, and hemoglobin values before and during the endurance ride. Each point represents the mean and the bars represent ± one standard deviation, and FIG. 2 represents photomicrographs (original magnification X1000) of erythrocytes from a blood smear of one horse showing normal erythrocytes at the control pre-ride sampling (A), and a predominance of spiculated erythrocytes after 91 kilometers of running (B). The scanning electron micrograph (C) (original magnification X5000) shows the morphology of the spiculated cells (N, normal erythrocyte; S, markedly spiculated erythrocyte; M, minimally spiculated erythrocyte).

Horses and ride conditions. Fourteen horses of various breeds (principally Arabian) were studied during the 1979 Old-Dominion 100-mile Endurance Ride in Northern Virginia. The actual distance of the ride was 97.4 mi (157 km). The horses were all well conditioned and 8 horses completed the ride. Finishing times ranged from 14 to 21 hours and included seven scheduled rest periods totaling four hours. At each rest stop, the horses were allowed electrolytes in the drinking water and food. The weather was clear and temperature and relative humidity ranged from 20.6° to 31.1° C. and 58 to 90 percent, respectively. The terrain varied from flat to mountainous.

Data and sample collection. Heart rates, respiratory rates, rectal temperatures and general condition of the horses were assessed by veterinary teams at all seven rest stops and the finish. Horses were eliminated if they were judged to have excessive fatigue, lameness, dehydration, or thermoregulatory problems.

Venous blood samples were obtained the day before the ride (control sample) and immediately upon entering the 44, 91 and 130 km rest stops and at the finish (157 km). Blood samples were collected in trisodium ethylenediaminetetraacetate (EDTA) to a final concentration of 1.5%, placed in an ice bath, and analyzed within two hours of collection.

Red cell studies. Hematocrits (HCT) were determined in quadruplicate using a microhematocrit centrifuge. Hemoglobin (Hb) was analyzed spectrophotometrically as cyanmethemlobin in a Microblook Analyzer (Carlo-Erbe, Milan, Italy). Erythrocytes were counted in a coulter Counter (Model $Z_B$, Hialeah, FL 33010) calibrated to suspensions of horse erythrocytes. Erythrocyte indices were calculated as follows:

$$\text{Mean corpuscular volume } (MCV, \text{ femtoliters}) = \frac{HCT \text{ (liter/liter)} \times 1000}{\text{Erythrocyte count } (10^{12}/\text{liter})}$$

$$\text{Mean corpuscular hemoglobin } (MCH, \text{ picograms}) = \frac{Hb \text{ (g/liter)}}{\text{Erythrocyte count } (10^{12}/\text{liter})}$$

$$\text{Mean corpuscular hemoglobin concentration } (MCHC, \text{ g/dl}) = \frac{Hb \text{ (g/dl)}}{HCT \text{ (liter/liter)}}$$

Because changes in mean erythrocyte count, hematocrit, and hemoglobin suggested possible intravascular hemolysis, previously prepared peripheral blood smears on 8 of the 14 horses were examined. Blood smears were stained with May-Grunwald Giemsa stain and examined under oil immersion (X1000) for morphological changes in the red cells. A large number of spiculated red cells were observed. Since morphological evaluation was done on dried blood films only and there was some discussion as to whether the observed cells were acanthocytes of echinocytes, the number of spiculated cells were determined without further classification. The spiculated cell counts were done by two different investigators without knowledge of the origin of the samples they were counting. Each investigator counted 100 cells in each of 5 different fields and classified the red cells as normal, minimally spiculated (at least 3 rounded spicules), or markedly spiculated (at least 5 sharp spicules). Cell counts were summed (1000 cells total) and the percent of normal, spiculated, and markedly spiculated cells were calculated.

Sections from selected blood smears were coated with gold-palladium (60:40) to a thickness of 125 angstroms. Coated specimens were examined in a scanning electron microscope (Advanced Metals Research Corp., Model 100, Bedford, MA 01730) and representative micrographs recorded on Polaroid film.

Statistical analyses. Mean and standard deviation was calculated and significant differences were determined by Student's paired t-test.

Heart rates and core temperatures. Mean heat rates and core temperatures of the horses before and during the endurance ride are given in Table 1. The mean heart rate at 44 km increased 93% above the resting level ($P<0.001$) and remained similarly elevated upon entering subsequent rest stops. The mean core temperature at 44 km increased 1.3° C. above resting values ($P<0.001$) and remained similarly elevated for the remainder of the ride. These changes were consistent with the strenuous, prolonged exercise to which the horses were subjected.

Erythrocyte counts, hematocrits and hemoglobins. Table 2 summarizes the results of erythrocyte counts, hematocrits, hemoglobins and determinations of erythrocyte indices performed before, during and after the endurance ride. Changes in mean erythrocyte count, hematocrit and hemoglobin over the course of the ride are more easily visualized graphically (FIG. 1). At 44 km, the first rest stop, there were marked increases in mean erythrocyte count (41%, $P<0.001$), HCT (30%, $P<0.001$) and Hb (33%, $P<0.001$). At subsequent rest stops and the finish, these values remained significantly elevated above controls but decreased from the 44 km values. At the finish, the mean HCT has decreased 9% ($P<0.01$) and mean Hb decreased 8% ($P<0.05$) from the 44 km values. The mean erythrocyte count at 130 km had decreased 8% ($P<0.05$) from the 44 km value, but the value at the finish was not statistically different from the 44 km value.

Erythrocyte indices. As shown in Table 2, there was a significant decrease in MCV at 44 km (8%, $P<0.001$) which persisted for the remainder of the ride. The MCH showed similar changes. The most marked changes in MCV (11% decrease, $P<0.001$, MCH (10% decrease, $P<0.001$) and MCHC (9% increase, $P<0.05$) occurred at the 91 km rest stop. This was the rest stop where the highest mean spiculated cell counts (Table 3) and the highest mean heart rate and core temperature (Table 1) were observed.

Red cell morphology. No schistocytes or other evidence of intravascular hemolysis were observed on examination of peripheral blood smears. Photomicrographs of blood smears from one of the horses are shown in FIG. 2. In the blood smear taken before the ride (FIG. 2(A)), spiculated cells were observed only rarely, whereas at the 91 km rest stop greater than 50 percent of the circulating erythrocytes were spiculated (FIG. 2(B)). The scanning electron micrograph shown in FIG. 2(C) illustrates that the spiculated cells exhibited varying degrees of spiculation. It should be noted that the scanning electron micrographs were of dried blood smears. The artifacts induced by drying of the red cells make the scanning electron micrographs less than optimal for the accurate determination of true red cell morphology.

Table 3 summarizes the spiculated cell counts during the endurance ride. The mean percent count of markedly spiculated and of total spiculated cells increased 9.4% and 18.2%, respectively, at 91 km ($P<0.005$). The mean spiculated cell counts at 130 and 157 km were not significantly different from control.

Erythrocyte count, hematrocrit, hemoglobin, and erythrocyte indices. Mean erythrocyte count, hematocrit and hemoglobin increased and followed roughly parallel courses during the prolonged endurance exercise of the ride. The increase in mean erythrocyte count was great (41%, $P<0.001$) at the 44 km rest stop than the increases in HCT (30%, $P<0.001$) and Hb (33%, $P<0.001$). This difference was reflected in the decreased MCV (8% decrease, $P<0.001$) and MCH (6% decrease, $P<0.05$) and is consistent with mobilization of a sequestered population of older, smaller erythrocytes from the spleen during exercise. A decrease in plasma volume due to dehydration probably plays a more minor role in the hemoconcentration that occurs with exercise.

At later rest stops, mean erythrocyte count, hematocrit, and hemoglobin values were decreased from the values at 44 km. This may reflect increased erythrocyte destruction with prolonged exercise. Such erythrocyte destruction has been observed in humans with prolonged, strenuous exercise.

The conditioned horses in this study had lower resting (control) HCT values (34.4±3.5%) than those reported for most Thoroughbred and Arabian horses. This finding agrees with observations of those who have reported that endurance trained horses, regardless of breed, had lower HCT values (35.0±2.5% and 36.3±2.9% respectively).

The conditioned horses in this study also had lower control MCV values (39.2±1.7 fl) than those reported for similar breeds.

Morphologic changes in erythrocytes. No fragmented cells (schistocytes) were observed to indicate extensive intravascular hemolysis with exercise. However, a marked increase in the number of spiculated cells in the peripheral blood was noted during exercise. The highest counts (22.0% markedly spiculated cells) were seen at the 91 km rest stop. The horses arrived at this rest stop after negotiating some of the more mountainous areas of the course during the hottest time of the day. The stress of this portion of the course was reflected in the highest mean heart rate and highest mean core temperature observed during the ride. The erythrocyte indices also showed the most marked changes at this rest stop. The MCV decreased 11% ($P<0.001$), MCH decreased 10% ($P<0.001$) and MCHC increased 9% ($P<0.05$) from control.

The finding of increases spiculated erythrocytes during the endurance ride was unexpected. No attempt was made to differentiate the spiculated cells as either echinocytes or acanthocytes because their morphology can appear similar when observed on a dried, stained peripheral blood film. Further, whether spiculated erythrocytes in horses are analogous to the acanthocytes and/or echinocytes observed in humans under various physiological and pathological conditions is uncertain.

In summary, a marked increase in the number of spiculated erythrocytes in the peripheral blood during prolonged endurance exercise in horses has been observed. The increased number of spiculated cells was accompanied by increases in the mean erythrocyte count, hematocrit, and hemoglobin and decreases in the MCV and MCH.

the boluses are administered to the horse with a balling-gun.

To insure that the number of crenated red blood cells in an otherwise healthy horse weighing 600 kilo and

TABLE 1

| | Heart rates and temperatures with exercise | | | | |
|---|---|---|---|---|---|
| | Control | 44 km | 91 km | 130 km | 157 km |
| Number of horses | 14 | 14 | 12 | 8 | 8 |
| Heart rate (beats/min) | 40 ± 4 | 77 ± 17* | 83 ± 14* | 74 ± 18** | 64 ± 17** |
| Core Temperature (°C.) | 37.7 ± 0.3 | 39.0 ± 0.6* | 39.5 ± 0.8* | 39.2 ± 0.8* | 39.2 ± 1.1* |

Values are means ± standard deviations.
Differences from control: *$P < 0.001$; **$P < 0.01$.

TABLE 2

| | Hematological values with exercise | | | | |
|---|---|---|---|---|---|
| | Control | 44 km | 91 km | 130 km | 157 km |
| Number of horses | 14 | 13 | 12 | 8 | 8 |
| Erythrocyte count ($10^{12}$/l) | 8.8 ± 1.0 | 12.4 ± 1.1* | 12.4 ± 1.3* | 11.4 ± 1.5*+++ | 11.4 ± 1.0* |
| Hematocrit (%) | 34.4 ± 3.5 | 44.7 ± 2.9* | 40.2 ± 6.0**++ | 40.5 ± 5.4*++ | 40.5 ± 3.5 |
| Hemoglobin (g/dl) | 14.9 ± 1.6 | 19.8 ± 1.5* | 18.9 ± 1.9*+++ | 18.4 ± 1.9*++ | 18.3 ± 1.1*+++ |
| MCV (fl) | 39.2 ± 1.7 | 36.2 ± 2.7* | 34.8 ± 2.3*+++ | 35.6 ± 1.7** | 35.5 ± 1.5** |
| MCH (pg) | 17.1 ± 1.9 | 16.1 ± 1.5*** | 15.4 ± 1.4*+++ | 16.3 ± 1.2*** | 16.1 ± 0.8*** |
| MCHC (g/dl) | 43.4 ± 4.3 | 44.3 ± 1.7 | 47.4 ± 4.6***+++ | 45.6 ± 2.2 | 45.3 ± 1.6 |

Values are means ± standard deviations. MCV, mean corpuscular volume; MCH, mean corpuscular hemoglobin; MCHC, mean corpuscular hemoglobin concentration.
Differences from control: *$P < 0.001$; $P < 0.01$; *$P < 0.05$.
Differences from 44 km: +$P < 0.001$; ++$P < 0.01$; +++$P < 0.05$.

TABLE 3

| | Spiculated erythrocyte counts with exercise | | | | |
|---|---|---|---|---|---|
| | Control | 44 km | 91 km | 130 km | 157 km |
| Number of horses | 8 | 8 | 7 | 6 | 2 |
| Markedly spiculated cells, % | 3.8 ± 3.6 | 13.2 ± 12.5** | 22.0 ± 11.5* | 14.1 ± 11.4 | 6.9 ± 3.3 |
| Total spiculated cells, % | 13.9 ± 9.3 | 32.1 ± 17.8** | 51.7 ± 20.5* | 38.2 ± 23.0 | 25.2 ± 9.1 |

Values are means ± SD.
Differences from control: *$P < 0.005$, **$P < 0.05$.

The following examples are given for illustration only and are not to be construed as limiting the invention or scope thereof in any way.

EXAMPLE I 100 boluses each containing as the active ingredient 500 mg of flunarizine are prepared from the following formulation:

| | Grams |
|---|---|
| Flunarizine | 50 |
| Starch | 75 |
| Dibasic calcium phosphate hydrous | 500 |
| Calcium stearate | 2.5 |

The ingredients are mixed well and granulated with 10% starch paste. The granulation is dried and compressed into boluses using starch as a disintegrant and calcium stearate as a lubricant. Appropriate number of the boluses are administered to the horse with a balling-gun.

To insure that the number of crenated red blood cells in an otherwise healthy horse weighing 600 kilo and having a normal resting red blood cell count of 8.75 ($10^{12}$/l blood) does not increase, the horse is fed 1 of the boluses daily for at least 7 days prior to a strenuous execising event in which optimal tissue oxygenation is imperative.

EXAMPLE II

Example I is repeated substituting cinnarizine for the flunarizine. Similar results are obtained.

It is claimed:

1. A method of treating a horse to prevent or reduce the increase in crenated red blood cells which occurs in the blood of said animal after exercise sufficient to induce said increase of crenated red blood cells, the blood of said animal having a normal content of crenated red blood cells prior to said exercise, which comprises administering to said animal immediately prior, during or subsequent to said exercise an effective amount of a compound which inhibits influx of extracellular $Ca^{++}$ ions into red blood cells.

2. A method according to claim 1 wherein the compound is lidoflazine.

* * * * *